United States Patent [19]

Ahad

[11] Patent Number: 4,891,438

[45] Date of Patent: Jan. 2, 1990

[54] DIRECT CONVERSION OF EPICHLOROHYDRIN TO GLYCIDYL AZIDE POLYMER

[75] Inventor: Elie Ahad, Ste-Foy, Canada

[73] Assignee: Her Majesty the Queen in right of Canada, as repesented by the Minister of National Defence of Her Majesty's Canadian Government, Ontario, Canada

[21] Appl. No.: 376,170

[22] Filed: Jul. 6, 1989

Related U.S. Application Data

[63] Continuation of Ser. No. 59,524, Jun. 8, 1987, abandoned.

[30] Foreign Application Priority Data

Dec. 1, 1986 [CA] Canada ................................. 524263

[51] Int. Cl.$^4$ .......................................... C07C 117/00
[52] U.S. Cl. ................................................. 552/11
[58] Field of Search .................................... 552/11

[56] References Cited

U.S. PATENT DOCUMENTS

| | | | |
|---|---|---|---|
| 1,971,662 | 8/1934 | Schmidt et al. | 568/614 X |
| 2,599,799 | 6/1952 | Wittcoff | 568/614 X |
| 3,875,189 | 4/1975 | Petty | 568/614 X |
| 4,268,450 | 5/1981 | Frankel et al. | 260/349 |
| 4,419,286 | 12/1983 | Witucki et al. | 260/349 |
| 4,486,351 | 12/1984 | Earl | 260/349 |

OTHER PUBLICATIONS

H138 United States Statutory Invention Registration, 10-7-86, Gilbert.

*Primary Examiner*—Joseph Paul Brust
*Attorney, Agent, or Firm*—Nixon & Vanderhye

[57] ABSTRACT

The invention disclosed is an improved process for the preparation of hydroxy-terminated aliphatic polyesters having alkyl substituents, such as glycidyl azide polymer. The improved process involves formation of the polymer in a single step starting from epichlorohydrin monomer. The reaction is effected in a suitable polar organic solvent at elevated temperature for 15 to 24 hours.

14 Claims, No Drawings

DIRECT CONVERSION OF EPICHLOROHYDRIN TO GLYCIDYL AZIDE POLYMER

This is a continuation of application Ser. No. 07/059,524, filed June 8, 1987, now abandoned.

This invention relates to an improved process for the synthesis of hydroxy-terminated aliphatic polyethers having alkyl azide substituents.

Hydroxy-terminated aliphatic polyethers having alkyl azide substituents are useful as energetic binders and plasticizers in solid propellants and composite explosives. One such polyether is glycidyl azide polymer (GAP). This polymeric azide is used as an energetic binder (at MW 2000–6000) and as a plasticizer (at MW of about 500) in composite explosives and solid rocket propellant systems to impart additional energy to the formulations, increase the performance and enhance the stability and the mechanical properties of the system.

A process for the preparation of hydroxy-terminated aliphatic polyethers having alkyl azide substituents, e.g. GAP, is described in U.S. Pat. No. 4,268,450 of May 19, 1981, in the name of M. B. Frankel et al. According to the Frankel et al process, in a first reaction step, the starting material, epichlorohydrin (ECH) ia polymerized to polyepichlorohydrin (PECH) using a catalyst, boron trifluoride (BF$_3$) in the presence of a dichloro compound such as carbon dichloride. In a second step, PECH is azidized using a molar excess of the order of 2:1 sodium azide (NaN$_3$) in the presence of a polar organic solvent dimethyl formamide (DMF) for three days at 100° C. It is emphasized that a molar excess, of about 2:1, of sodium azide is typically employed. Since sodium azide is of a poisonous nature, the use of large amounts is a distinct disadvantage. A final purification step using methylene chloride and drying over magnesium sulfate is also described. This multi step process is costly and takes from four to seven days to complete.

According to the invention, a single step process for the preparation of hydroxy-terminated polyethers having alkyl azide substituents, e.g. GAP, is provided which is less time consuming and more cost effective.

The process according to the invention for the preparation of hydroxy-terminated aliphatic polyethers having alkyl azide substituents, having a structural formula

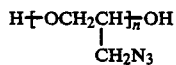

wherein n is an integer from 5 to 10, comprises the single step of reacting epichlorohydrin monomer (ECH) with an ionic azide, selected from the group consisting of sodium azide, lithium azide and potassium azide, in a suitable polar organic solvent at elevated temperature for about 15 to 24 hours, while agitating.

The preferred ionic azide is sodium azide. Preferably, the weight ratio of sodium azide to ECH is about 1:1.

Suitable polar organic solvents include dimethyl formamide (DMF), and dimethyl sulfoxide (DMSO). A small amount of ethylene glycol (EG) is used as an initiator.

The reaction temperature is typically in the range of 70° to 90° C., with a temperature of about 90° C. being preferred.

More preferably, an initial exothermic reaction is allowed to proceed at a temperature of about 70° C., followed by heating to about 90° C. to complete the reaction. Specifically, the exothermic reaction arises from the opening of the epoxide ring of ECH which is caused by sodium azide and proceeds for about thirty minutes. The "30 minutes" period is approximate and depends on the duration of the gradual addition of sodium azide to the mixture ECH/DMF/EG. It is preferable to heat the reaction mixture at 70° C. (approx) during the addition of NaN$_3$ in order to control the exothermic reaction. Once the sodium azide addition is over and no sudden rise in temperature is observed, then heating to 90° C. starts.

Preferably upon cooling, the polymer is washed with water to remove DMF, EG, unreacted sodium azide and the by-product sodium chloride. Three washes with hot water (60° C.) have been found appropriate.

Preferably, the washing step is followed by a purification step which involves dissolving the polymer in a suitable polar organic solvent such as methylene chloride, drying over magnesium sulfate, and passing through a column containing silica gel. The solvent is then driven off by heating.

As shown in Table I below, the synthesis of GAP according to the invention can be accomplished at about 90° C. in about 15 hours or in 24 hours by using less solvent (DMF/ECH=0.8). At a reaction temperature lower than 90° C., the quantitative conversion of ECH to GAP will require a much longer reaction time, e.g. 48 hours at 80° C. and 170 hours at 70° C.

TABLE I

| T (°C.) | reaction time (hours) | $\left(\dfrac{DMF}{ECH}\right)$ |
|---|---|---|
| 90 | 15 | 2.0 |
| 90 | 24 | 0.8 |
| 80 | 48 | 2.0 |
| 70 | 170 | 2.0 |

The hydroxy-terminated aliphatic polyethers having alkyl azide substituents prepared according to the invention are of the lower molecular weight (i.e., average MW of about 500 and n=5 to 10) variety described above.

EXAMPLE

Sodium azide (10 g) is gradually added to a mixture of ECH (10 g), DMF (20 g) and EG (1 g); heating at approximately 70° C. and agitation are started. Because of an initial exothermic reaction, the temperature is controlled during the first 30 minutes (approx) of the synthesis. Once the addition of sodium azide is over and no sudden rise in temperature is observed, then the reaction mixture is heated to 90° C. and the agitation is carried out at this temperature for about 15 hours. Heating and agitation are stopped and the reaction mixture is allowed to cool. The polymer is given three 50 ml hot water (60° C.) washes to remove DMF, EG and the salts (sodium azide and sodium chloride). The polymer is dissolved in 75 ml methylene chloride (MC). The MC solution is dried over magnesium sulfate and then is passed through a column containing 5 g of silica gel. The resultant solution is heated to 50° C. to remove MC and then stripped in vaccuo to yield 8 g (80%) of the GAP polymer: a viscous liquid with an amber colour. The GAP was characterized and had the following properties:

Elemental Analysis

C(35.7); H(5.0); N(39.9); O(18.7); Cl(0.7) wt%

Nitrogen and Chloride analysis of the polymer confirmed that quantitative conversion of ECH to GAP was achieved.

Infrared Spectrum

The IR absorption spectrum of the polymer showed peaks at 4.8 and 8.0 m$\mu$ (characteristics of azides).

| | |
|---|---|
| Weight Average Molecular Weight (Mw) | 540 |
| Number Average Molecular Weight (Mn) | 400 |
| Equivalent Weight (Me) | 314 |
| Glass Transition Temperature (Tg) | −70° C. |
| Density | 1.3 g/ml |
| Hydroxyl Functionality (Mn/Me) | 1.3 |

Other similar hydroxy-terminated aliphatic polyethers having alkyl azide substituents may be prepared in a similar manner by employing other representative epoxides such as 2,3-epoxybutane and isobutylene oxide, as the starting material.

The embodiments of the invention in which an exclusive property or privilege is claimed is defined as follows:

1. A process for the preparation of a hydroxy-teminated aliphatic polyether having alkyl azide substitutents, having a structural formula:

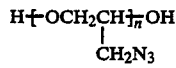

wherein n is an integer from 5 to 10, consisting essentially of the single step of reacting epichlorohydrin with an ionic azide, selected from the group consisting of sodium azide, potassium azide and lithium azide, in a suitable polar organic solvent at elevated temperature for about 15 to about 24 hours, while agitating, to directly prepare a hydroxy-terminated aliphatic polyether.

2. A process as claimed in claim 1, wherein the elevated temperature is about 70° C.–90° C.

3. A process as claimed in claim 2, wherein the organic solvent is selected from the group consisting of dimethyl formamide and dimethyl sulfoxide.

4. A process as claimed in claim 3, wherein the organic solvent is dimethyl formamide.

5. A process as claimed in claim 4, wherein the ionic azide is sodium azide.

6. A process as claimed in claim 5, wherein ethylene glycol is included as initiator.

7. A process as claimed in claim 6, including the additional step of washing the polymer so formed with water.

8. A process as claimed in claim 7, including the further additional step of purifying the polymer by dissolving the washed polymer in a suitable polar organic solvent, drying over magnesium sulfate and passing through a column containing silica gel.

9. A process as claimed in claim 6, wherein during the addition of sodium azide heating is effected to about 70° C. to control the initial exothermic reaction, followed by heating to about 90° C. to complete the reaction.

10. A process as claimed in claim 9, wherein the ratio of dimethyl formamide to epichlorohydrin is about 2:1 and wherein the reaction time is about 15 hours.

11. A process as claimed in claim 9, wherein the ratio of dimethyl formamide to epichlorohydrin is about 0.8:1 and wherein the reaction time is about 24 hours.

12. A process as claimed in claim 5, wherein the weight ratio of sodium azide to epichlorohydrin is about 1:1.

13. A process as claimed in claim 10, wherein the weight ratio of sodium azide to epichlorohydrin is about 1:1.

14. A process as claimed in claim 11, wherein the weight ratio of sodium azide to epichlorohydrin is about 1:1.

* * * * *